US005942231A

United States Patent [19]

Hamada et al.

[11] Patent Number: 5,942,231

[45] Date of Patent: Aug. 24, 1999

[54] METHOD OF TREATMENT OF ATOPIC DERMATITIS WITH DRIED GUAVA LEAVES

[75] Inventors: Sadao Hamada, Arakawa-ku; Susumu Kitanaka, Narashino, both of Japan

[73] Assignee: O.S. Industry Co., Ltd., Tokyo, Japan

[21] Appl. No.: 08/664,920

[22] Filed: Jun. 18, 1996

[30] Foreign Application Priority Data

Jun. 20, 1995 [JP] Japan .................................... 7-176741

[51] Int. Cl.$^{6}$ ..................................................... A01N 65/00

[52] U.S. Cl. ....................... 424/195.1; 514/885; 514/826; 514/861; 514/863; 514/864

[58] Field of Search ......................... 424/195.1; 514/885, 514/826, 861, 863, 864

[56] References Cited

U.S. PATENT DOCUMENTS 5,066,671 11/1991 Caufield .................................. 514/453

FOREIGN PATENT DOCUMENTS

A-0 154 530 9/1985 European Pat. Off. ....... A61K 35/78

OTHER PUBLICATIONS

Davis et al., Microbiology, 1990, p. 415, Lippincott Co.

Pulido et al., 1993, Lista Anotada de las Plantas Medicinales de Uso Actual en el Estado de Quintana Roo, Mexico. p. 46.

Patent Abstracts of Japan, vol. 18, No. 1 (C–1148)(1994).

Patent Abstracts of Japan, vol. 9, No. 188 (C–295) (1985).

European Patent Office Database WPI, Week 9538, Derwent Publications Ltd.

*Primary Examiner*—Irene Marx

*Attorney, Agent, or Firm*—David G. Conlin; Peter F. Corless; Dike, Bronstein, Roberts & Cushman, LLP

[57] ABSTRACT

A method of treating a patient suffering from allergic diseases, comprises administering to said patient an effective amount of a pharmaceutical composition in dosage unit form comprising a dry powder of guava leaves.

3 Claims, No Drawings

METHOD OF TREATMENT OF ATOPIC DERMATITIS WITH DRIED GUAVA LEAVES

BACKGROUND OF THE INVENTION

The present invention relates to a method of treatment of allergic diseases, and more particularly it relates to a method of treating a patient suffering from allergic diseases, which comprises administering to said patient an effective amount of a pharmaceutical composition in dosage unit form comprising a dry powder of guava leaves or an extract obtained from guava leaves by a solvent.

Recently, the allergic diseases such as bronchial asthma, atopic dermatitis, allergic rhinitis and pollenosis are increasing. These allergic diseases are, in most cases, traceable to the I type allergic reaction, and it is known that the allergic diseases are induced by the liberation of a chemical transfer substance which takes place when an immunoglobulin E antibody against allergen, which has been produced in large, is combined with allergen on the surfaces of the mast cells.

Hitherto, steroidal preparations have been generally used as therapeutic agents for allergic diseases, but such steroidal preparations have strong side-effects and require circumspection for their application.

Guava (botanical name: *Psidium guajava* L.) is a plant belonging to the family Myrtaceae, which is native to South America. This plant has been known from long ago as a medicinal tree, and its leaves have been used as a salve for wounds and a medicine for the stomach and bowels. The solvent extract obtained from the guava leaves are also used for cosmetics (see Japanese Patent Application Laid-Open (Kokai) No. 5-245837). However, it has not been known that the guava leaves have an antiallergic activity.

As a result of the present inventors' extensive researches of screening of the available medicinal plants for solving the above-mentioned problems, it has been found that a dry powder of guava leaves or a solvent extraction obtained from the guava leaves has an antiallergic activity. The present invention has been attained on the basis of this finding.

SUMMARY OF THE INVENTION

It is an object of the present invention to provide a therapeutic agent for allergic diseases which has no side effects.

To accomplish the aim, in the first aspect of the present invention, there is provided a method of treating a patient suffering from allergic diseases, which comprises administering to said patient an effective amount of a pharmaceutical composition in dosage unit form comprising a dry powder of guava leaves.

In the second aspect of the present invention, there is provided a method of treating a patient suffering from atopic dermatitis diseases, which comprises administering to said patient an effective amount of a pharmaceutical composition in dosage unit form comprising a dry powder of guava leaves.

In the third aspect of the present invention, there is provided a method of treating a patient suffering from allergic diseases, which comprises administering to said patient an effective amount of a pharmaceutical composition in dosage unit form comprising an extract obtained from guava leaves by a solvent.

In the fourth aspect of the present invention, there is provided a method of treating a patient suffering from atopic dermatitis diseases, which comprises administering to said patient an effective amount of a pharmaceutical composition in dosage unit form comprising an extract obtained from guava leaves by a solvent.

DETAILED DESCRIPTION OF THE INVENTION

The present invention is described in detail below.

Since guava (botanical name: *Psidium guajava* L.) is widely cultivated, the guava leaves are easily available. It is preferable, however, to use the leaves of wild-grown guava.

The leaves of guava are dried and then pulverized to obtain a dry powder. Drying and pulverization can be accomplished by the conventional methods. As for drying, natural drying with no specific heat applied is preferred. The degree of pulverization may be properly selected in accordance with the formulation of the medicine. For instance, in case where the dry powder is blended in a cream base, the guava leaves are pulverized to such an extent as to provide a powder with an average particle size not more than 0.3 mm, preferably 1 to 30 $\mu$m. In case where the dry powder is contained in a water-permeable bag and used as a balneotherapy agent, the guava leaves are pulverized to such an extend as to provide a 40- to 80-mesh powder.

The guava leaf extract can be obtained by extracting said dry powder with a solvent and removing the solvent from the liquid extract by suitable means such as concentration under reduced pressure, etc. As solvent for the said extraction, there can be used water, alcohols such as methanol and ethanol, acetone and mixtures thereof. Alcohols and acetone are preferred. The obtained extract may, if necessary, be further purified by conventional means such as column chromatography.

The thus obtained extract usually has the following properties:

(1) It is reacted with a ferric salt to assume a dark blue or dark green color;

(2) It is reacted with chromic acid or a chromate and is precipitated; and (3) It is reacted with potassium ferricyanate and ammonia and to assume a deep red color.

Dry powder of guava leaves obtained in the manner described above can be directly applied to the diseased part, but usually it is processed into a medicinal preparation according to the conventional methods. The solvent extract of said dry powder is also usually processed into a medicament. In forming such medicaments, various kinds of adjuvants normally used in preparation of the drugs, for example, carriers such as distilled water, white vaselines, and other additives such as stabilizers, antiseptics, emulsifiers, etc., may be incorporated thereinto as occasion demands. The dosage forms of medicaments contemplated in the present invention include tablet, powder, granule, liquid, lotion, suspension, cream, ointment, spray, balneotherapy agent and the like. A pertinent form is selected in view of the way of administration or application. For example, in the case of external application, such dosage form as liquid, lotion, suspension, cream, ointment, spray, balneotherapy agent or the like may be selected.

The amount of the dry powder in the preparations is usually 2 to 30% by weight, preferably 5 to 15% by weight. The amount of the extract in the preparation is usually 1 to 20% by weight, preferably 2 to 5% by weight.

As for the way of administration of the therapeutic agent for allergic diseases according to the present invention, the agent is usually administered orally, externally (locally), or by means of inhalation or aeration, or by a combination thereof. The external administration is recommended for treating the allergic diseases of the present invention. The dosage amount is variable depending on the way of application. In the case of external administration, for instance, a preparation containing 5 to 15% by weight of the said dry powder or 2 to 5% by weight of the said extract is administered to the affected part once to several times per day. In the case of oral administration, the preparation is administered once to several times per day at a dose of 0.3–0.5 g for the dry powder and 10 to 25 mg for the extract for adults.

The therapeutic agent for allergic diseases used in the present invention is also suited for use as a balneotherapy agent. This balneotherapy agent can be produced by containing said dry powder of guava leaves in a water-permeable bag. The material of the water-permeable bag may be properly selected in consideration of the particle size of the powder to be contained and other factors, but it is recommended to use a material with high strength since physical forces such as generated by rubbing are exerted to the bag in use. A typical example of such water-permeable material is nonwoven fabric cloth such as nylon gauze. The amount of the powder to be contained in one bag is preferably such that will be needed for one bath. The amount of the powder suited for one bath is usually 10 to 15 g in the case of domestic bathtub (180–220 liter). The thus prepared balneotherapy agent is usually kept in a bag made of a light-shielding air-proof material such as PET-aluminum composite material for preventing deterioration of the powder by oxidation or other causes. In use, this balneotherapy agent is put into bathwater when one takes a bath, and it may be left in bathwater during bathing. Also, the contents of the bag may be properly rubbed out into bathwater.

The above-shown dosage and way of administration are variable depending on the various factors such as age and gender of the patient, condition and degree of the disease, use of other medicine(s), etc.

The therapeutic agent for allergic diseases used in the present invention shows a prominent therapeutical effect particularly against atopic dermatitis. It is considered that such a therapeutical effect is attributable to its histamine release inhibiting activity which has been confirmed in a histamine release inhibition test using the mast cells. Therefore, the agent used in the present invention is expected to be applicable not only to atopic dermatitis but also to other allergic diseases associated with histamine, such as bronchial asthma, allergic rhinitis and pollenosis.

Medical decoctions of guava leaves have been habitually taken by many people for long, and therefore, the safety of guava leaves has empirically been confirmed.

Thus, according to the present invention, there are provided a therapeutic method of allergic diseases with few side effects and therapeutics for allergic diseases using said agent.

EXAMPLES

The present invention is explained in more detail in the following examples, which examples however are presented for illustrative purposes only and should not be construed as limiting the scope of the invention.

Test Example 1

5.8 kg of dry guava leaves were subjected to three times of extraction treatment with 5 liters of 80% hydrous acetone at room temperature irradiating an ultrasonic ray and the resulting liquid extract was concentrated under reduced pressure to obtained 306.4 g of extract.

To 306 g of the obtained extract was added one liter of water, and the resultant solution was passed through a column (11.5 cm×25 cm) packed with water-prepared Diaion HP-20 (trade name). The extract was eluted with a water-methanol mixed solvent while increasing the methanol concentration (0 to 100% v/v). The final elution was conducted with acetone to obtain eight fractions as shown in Table 1. The histamine release inhibiting activity of each of the thus obtained fractions was determined by a bioactivity assay method. The results are also shown in Table 1.

TABLE 1

| Fraction | Solvent | Yield (g) | Histamine release inhibition (%) |
|---|---|---|---|
| 1 | water | 39.200 | 23 |
| 2 | methanol/water (1:9) | 30.434 | 105 |
| 3 | methanol/water (2:8) | 28.150 | 105 |
| 4 | methanol/water (4:6) | 28.777 | 97 |
| 5 | methanol/water (7:3) | 9.795 | 95 |
| 6 | methanol/water (1:9) | 8.542 | 59 |
| 7 | methanol | 3.517 | 33 |
| 8 | acetone | 1.234 | 25 |

Bioactivity assay method (1) Preparation of rat abdominal mast cell suspension

The 7- to 8-week old Wistar rats were depleted to death under etherization. Immediately thereafter, 20 ml of Tyrode's solution was injected into the abdominal cavity of each rat, followed by approximately 3-minute massage of the abdominal cavity. Then abdominal dropsy was drawn out and centrifuged at 4° C. and 150× g for 10 minutes, and the precipitated cells were collected. The cells were suspended in 2 ml of Tyrode's solution, layered over 4 ml of a bovine serum albumin (BSA) solution with a specific gravity of 1.068 and centrifuged at 4° C. and 100× g for 15 to 20 minutes, thereby causing the mast cells to precipitate. The collected precipitate was washed twice with 4 ml of Tyrode's solution and finally suspended in 1 ml of Tyrode's solution containing 0.2% of BSA to prepare a cell suspension (cell population: $1\times10^6$ cells/ml; about 80 to 90% of the whole cells are mast cells). The mast cells were counted by phase-contrast microscopical observation.

(2) Determination of inhibiting activity against histamine release from mast cells Each specimen was dissolved in a 0.5% dimethyl sulfoxide- 0.02 M phosphate buffer solution (pH 7.0) (PBS) to a constant concentration, and 100 μl of the cell suspension was added to 1 μl of this solution and heated at 37° C. for 5 minutes. 40 μl of the resulting solution was respectively supplied into two sampling tubes wherein 10 μl of PBS which contains a compound 48/80 in a concentration of 5 μg/ml are charged thereinto and two sampling tubes wherein 10 μl of PBS are charged thereinto, and incubated at 37° C. for 10 minutes. The sampling tubes were dipped into icy water to stop the reaction. Then the resultant solution was centrifuged under the conditions of 4° C. and 1,500× g for 4 minutes, and 30 μl of the obtained supernatant was collected. To this supernatant was added 30 μl of 0.1 M hydrochloric acid, followed by stirring. 10 μl of the resulting solution was injected into a HPLC column and assayed under the following conditions. The histamine release inhibiting ratio was calculated in contrast with the case using a 0.5% dimethyl sulfoxide-0.2 M phosphate buffer solution (pH 7.0) (PBS) alone being taken as control.

(3) Histamine assay by HPCL

Histamine assay by on-column HPLC was carried out according to Saito et al method (J. Chromatogr., 595, 163 (1982)). The HPLC conditions were as follows:

Column: Asahi-Pack ODP-50 (1.6 mm (ID)×250 mm)

Column temp.: 40° C.

Eluent: acetonitrile-50 mM sodium borate (18:82) (containing 1 mM each of o-phthalaldehyde and N-acetylcystine)

Flow rate: 0.5 ml/min

Detection: Ex.: 340 nm; Em.: 450 nm

Example 1

Guava leaves were dried in the shade and powdered (average size: about 40–80 mesh size) by a pulverizer. 15 g of this powder was contained in each of the nylon gauze bags (Unicel BP-65W (trade name), produced by Teijin Co., Ltd.; 100 mm×120 mm) to obtain a bagged balneotherapy agent. The bags containing the balneotherapy agent were each kept in a sealed PET aluminum bag until put to use.

The results of the balneotherapy conducted by using said balneotherapy agent are shown below. In this balneotherapy, the patient was asked to bathe everyday in a domestic bathtub (180–220 liter) having one or two of said bags of balneotherapy agent placed in bathwater. Bathwater was replaced everyday.

Example 2

<Effect on atopic dermatitis in 23 year-old woman>

The patient suffering from atopic dermatitis had been taking a treatment for improving the condition by administering a steroid agent, but she has developed exanthemata on the face and over a wide region of her body, which was attended by a great deal of itch. Administration of a steroid agent to this patient was abandoned, and instead she was subjected to said balneotherapy using the balneotherapy agent obtained in Example 1. As a result, there took place in 2 to 3 days a phenomenon of "rebound" due to discontinuance of administration of the steroid agent, which caused a temporary swelling of the patient's face and an increase of eczema. However, the swelling subsided in two weeks, and eczema on the whole body began to decrease rapidly after the elapse of one month. In three months, the parts affected with eczema dried up, and both redness and moistness disappeared. In six months, eczema on the whole body has almost gone along with itch although slight remnants of eczema were still noted on the back.

Example 3

<Effect on infant atopic dermatitis in one-year-old boy>

The patient has developed moist eczema at the chin at three months after birth. In an allergy test conducted six months after birth, he showed an allergic reaction of 100% on egg, 100% on cow's milk and 55% on wheat. In view of this, it was tried not to give these foods to the infant to avoid occurrence of allergy. However, since abandonment of these foods is detrimental to the normal growth of the infant, it was decided to let him take these foods again four months later. In this situation, when breast milk was given to him, he developed moist eczema all over the body, causing severe itch and moistness again. The balneotherapy was conducted on this patient using the balneotherapy agent obtained in Example 1. The eczema began to reduce in two weeks, initially from the head and then from the face, the jaws and the body successively. In about two months, the infant's dermal condition has recovered to an extent almost equal to the normal skin excepting the part where the diaper was applied. Itch has also gone. The patient was making satisfactory progress ever since.

Example 4

<Effect on atopic dermatitis in 49 year-old woman>

The patient has been hypersensitive on the skin, showing for example high susceptibility to prickly heat, since her infant-hood. She began to feel itchy all over the body, had edemata in her legs and suffered an abnormal rise of allergic sensitivity. These symptoms were of seasonal nature, that is, abnormal itching of the body and exanthem would occur periodically from early spring into autumn every year. The balneotherapy was conducted on this patient using the balneotherapy agent obtained in Example 1, and as a result, itching of the body lessened greatly and her complexion became fresh in one month. Also, the chloasmata of the size of a 10-yen coin (diameter: about 23 mm) on both cheeks have almost disappeared. Thereafter, she has never complained abnormal itch on her body and retained a good condition ever since.

Example 5

Dry powder of guava was added to ethanol in an amount of 2% by weight, and the resultant mixture was left at room temperature for 12 hours to obtain an extract. The obtained extract was filtered and diluted 5-fold (v/v) with distilled water to obtain a liniment. A therapeutic treatment for atopic dermatitis conducted by using this liniment and its result are described below.

Example 6

<Treatment on atopic dermatitis in 15 year-old woman>

The patient had inflammation at her neck and around her eyes. She has developed exanthemata attended by severe itch at her neck throughout the year and around her eyes in the summer season. The liniment obtained in Example 5 was administered to the affected parts of the patient twice a day (in the morning and evening). In about one week after the treatment, itch has gone, and in three weeks, inflammation around the eyes has disappeared and also tetter at the neck has almost vanished, recovering the normal skin at the affected parts.

Example 7

Guava leaves were dried in the shade and powdered (average particle size: 0.01–0.03 mm) by a pulverizer. A therapeutic treatment for atopic dermatitis conducted by using this powder and its result are described below.

Example 8

<Effect on atopic dermatitis in 38 year-old man>

The patient had many exanthemata attended by itch at the upper arms, knees and neck. Many small vesicles were also seen at the affected parts. The condition was bad particularly in the period from spring to autumn, and even bleeding would be caused due to scratching of the affected parts. Also, the administration of a steroid agent has produced the side effect of blackening the skin at the neck and making it hirsute. The steroid administration on this patient was abandoned, and instead the powder obtained in Example 7 was directly applied to the affected parts twice a day (in the morning and evening) while at the same time conducting the balneotherapy using the balneotherapy agent obtained in Example 1 on the patient. As a result, in three days, moistness of the blended and blistered parts was greatly improved, and the skin was brought into a dried-up state. In one month, although the patient still complained a slight degree of itch at the neck, the skin was recovered to an extent identical with the normal skin, and the moist vesicles and itch have also gone.

Example 9

Dry powder of guava was added to white vaseline in an amount of 20% by weight and uniformly mixed to form a cream. A therapeutic treatment for atopic dermatitis using this cream and its result are described below.

Example 10

<Effect on atopic dermatitis in 30 year-old woman>

The patient was suffering from atopic dermatitis with many exanthemata at the regions from the shoulders to the front part of the neck. In the summer season, because of perspiration, the condition was too bad with many exanthemata and severe itch. The similar situation was seen when the body was warmed up after bathing. The cream obtained in Example 9 was applied to the affected parts of this patient three times a day (once after bathing). This treatment, particularly after bathing, worked marvelously in reducing exanthemata and alleviating itch, and it was confirmed that redness of the skin at the affected part reduced in about one week after start of the administration. Thereafter, in about one week, itch has almost gone although there still slightly remained eczema, and in two weeks, the skin at the affected part was substantially cleared of exanthemata and recovered to an extent equal to the normal skin. The treatment by administration of said cream is expected to take effect in a short time.

What is claimed is:

1. A method of treating atopic dermatitis in a patient suffering from atopic dermatitis, which comprises administering balneotherapeutically to the patient a pharmaceutical composition comprising an effective amount of dried guava leaves to relieve symptoms of atopic dermatitis, and the balneotherapeutic regimen comprises daily bathing in a bathtub.

2. A method of claim 1 wherein the dry powder of guava leaves are contained in a water-permeable bag, and the bag is placed in the bath.

3. A method of claim 1 wherein the effective amount of the dry powder of guava leaves is about 10 to 15 grams of the dry powder of guava leaves contained in a water-permeable bag are placed in a bathtub of about 180–220 liters of water in the bathtub.

* * * * *